United States Patent
Zhong

(10) Patent No.: US 8,263,103 B2
(45) Date of Patent: Sep. 11, 2012

(54) MEDICAL ARTICLES CONTAINING BIODEGRADABLE POLYMERS AND ACID-NEUTRALIZING CATIONIC SPECIES

(75) Inventor: Sheng-Ping Zhong, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 391 days.

(21) Appl. No.: 11/343,628

(22) Filed: Jan. 31, 2006

(65) Prior Publication Data

US 2007/0178135 A1    Aug. 2, 2007

(51) Int. Cl.
  *A61F 2/00*   (2006.01)
(52) U.S. Cl. .................................... 424/423
(58) Field of Classification Search .................. None
  See application file for complete search history.

(56) References Cited

U.S. PATENT DOCUMENTS

| | | | |
|---|---|---|---|
| 4,631,337 A | 12/1986 | Tomalia et al. | 528/391 |
| 5,714,166 A * | 2/1998 | Tomalia et al. | 424/486 |
| 5,731,095 A | 3/1998 | Milco et al. | 428/482 |
| 5,830,730 A | 11/1998 | German et al. | 435/172.3 |
| 5,834,020 A | 11/1998 | Margerum et al. | 424/484 |
| 6,127,448 A | 10/2000 | Domb | 523/105 |
| 6,262,162 B1 | 7/2001 | Lan et al. | 524/445 |
| 6,440,405 B1 | 8/2002 | Cooper et al. | 424/78.17 |
| 6,699,504 B2 * | 3/2004 | Rowe et al. | 424/486 |
| 6,743,521 B2 | 6/2004 | Hubbell et al. | 428/500 |
| 7,135,038 B1 * | 11/2006 | Limon | 623/1.15 |
| 2002/0041862 A1 | 4/2002 | Prusiner et al. | 424/78.27 |
| 2003/0124368 A1 | 7/2003 | Lynn et al. | 428/483 |
| 2003/0129158 A1 | 7/2003 | Matthews et al. | 424/78.17 |
| 2003/0134810 A1 * | 7/2003 | Springate et al. | 514/44 |
| 2003/0180250 A1 | 9/2003 | Chauhan et al. | 424/78.05 |
| 2003/0190364 A1 * | 10/2003 | Panitch et al. | 424/488 |
| 2003/0236514 A1 | 12/2003 | Schwarz | 604/890.1 |
| 2004/0076661 A1 * | 4/2004 | Chu et al. | 424/443 |
| 2004/0120979 A1 | 6/2004 | Roessler et al. | 424/426 |
| 2005/0027064 A1 | 2/2005 | Lynn et al. | |
| 2005/0187146 A1 | 8/2005 | Helmus et al. | |
| 2005/0278015 A1 * | 12/2005 | Dave et al. | 623/1.38 |

OTHER PUBLICATIONS

Anna U. Bielinska et al., "Application of membrane-based dendrimer/DNA complexes for solid phase transfection in vitro and in vivo," *Biomaterials*, vol. 21 (2000), pp. 877-887.

Dusko Cakara et al., "Microscopic Protonation Equilibria of Poly(amidoamine) Dendrimers from Macroscopic Titrations," *Macromolecules*, vol. 36 (2003), pp. 4201-4207.

Wei Lin et al., "Charging and Aggregation of Latex Particles by Oppositely Charged Dendrimers," *Langmuir*, vol. 20 (2004), pp. 7465-7473.

Ulrik Boas et al., "Dendrimers in drug research," *Chem. Soc. Rev.*, vol. 33 (2004), pp. 43-63.

Barbara Klajnert et al., "Dendrimers: properties and applications," *Acta Biochimica Polonica*, vol. 48, No. 1 (2001), pp. 199-208.

Ragheb Abu-Rmaileh et al., "Dendrimers in cancer research," *Drug Delivery Systems and Sciences*, vol. 3, No. 3 (2003), pp. 65-70.

F. Aulenta et al., "Dendrimers: a new class of nanoscopic containers and delivery devices," European Polymer Journal, 2003, 39: 1741-1771.

* cited by examiner

*Primary Examiner* — Paul Dickinson

(74) *Attorney, Agent, or Firm* — Mayer & Williams PC; David B. Bonham; Keum J. Park

(57) ABSTRACT

According to an aspect of the present invention, medical articles are provided, which are at least partially biodegradable. The medical articles comprise (a) biodegradable polymers that produce acidic molecules upon degradation; and (b) acid neutralizing cationic species.

23 Claims, No Drawings

MEDICAL ARTICLES CONTAINING BIODEGRADABLE POLYMERS AND ACID-NEUTRALIZING CATIONIC SPECIES

FIELD OF THE INVENTION

The present invention relates generally to medical articles, and more particularly to medical articles which contain biodegradable polymers.

BACKGROUND OF THE INVENTION

Many biodegradable polymers used in medical articles degrade through hydrolytic mechanisms. Common examples of such biodegradable polymers are poly(hydroxy acids) such as polylactide, polyglycolide, poly(lactide-co-glycolide) and polycarprolactone, polyanhydrides, and polyarylates, among others. The degradation byproducts produced by such polymers are frequently acidic, which may create a low pH environment in and around the polymer and result in an inflammatory response.

Acidic degradation byproducts may also have a profound effect on how the devices degrade. For example, it is known that polylactide, polyglycolide, poly(lactide-co-glycolide) display self-catalytic activity when they degrade in aqueous environments. In this regard, it is believed these polymers degrade in the bulk such that degradation byproducts are entrapped, thereby creating a low pH environment, which causes the biodegradation of the polymers to accelerate. This phenomenon can cause the devices to degrade into an empty shell under certain conditions, particularly where the device is sufficiently thick and has sufficient water permeability. Unfortunately, this type of degradation is an inferior degradation mechanism for certain applications, such as biodegradable stents. To prevent fragmentation of medical articles at a late stage of use, it is typically preferred that surface erosion be the prime mechanism for degradation.

Furthermore, in applications where therapeutic and diagnostic agents are included within matrices formed using biodegradable polymers, low pH environment may also be of concern if the agents are sensitive to acidic conditions (e.g., where a low pH environment may cause structural changes to the agents).

SUMMARY OF THE INVENTION

According to an aspect of the present invention, medical articles are provided which comprise (a) biodegradable polymers that produce acidic molecules upon degradation; and (b) acid neutralizing cationic species.

An advantage of such medical articles is that they may prevent adverse responses, including inflammatory responses, which would otherwise occur in the absence of such cationic species Another advantage of such medical articles is that they may prevent self-catalytic activity, which would otherwise occur in the absence of such cationic species.

Another advantage of such medical articles is that they may prevent harm to acid-sensitive therapeutic and diagnostic agents, which would otherwise occur in the absence of such cationic species.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention. The scope of the invention is defined by the appended claims.

As used herein, "polymers" are molecules that contain multiple constitutional units, commonly referred to as monomers. For example, polymers may contain, 2, 3, 4, 5, etc. monomers, commonly 10 or more monomers, 100 or more monomers, or 1000 or more monomers, with no upper limit, other than that imposed by technological hurdles. Polymers may contain multiple copies of a single type of monomer, in which case they are referred to herein as "homopolymers," or they may contain multiple copies of two or more types of monomers, in which case they are referred to herein as "copolymers." Dissimilar monomers within copolymers may be present in any of a variety of distributions including random, statistical, gradient and periodic (e.g., alternating) distributions, among others. Polymers containing two or more differing polymer segments are referred to herein as "block copolymers."

As used herein a "polymeric region" is a region that contains one or more types of polymers. Polymeric regions in accordance with the invention will commonly contain 50 wt % to 75 wt % to 90 wt % or more polymers.

The present invention is directed to medical articles which contain biodegradable polymers. As noted above, biodegradable polymers are widely used in medical articles such as absorbable sutures, bone screws, temporary bone fixation plates, controlled drug release microspheres, and they have more recently been used in guide tubes for nerve regeneration, scaffolding for tissue engineering, coatings for stents, and total absorbable stents, among other applications.

Unfortunately, the acidity of the degradation products (also referred to herein as "acidic degradants") of many biodegradable polymers introduces severe inflammation to certain tissue such as vascular tissue, and has therefore precluded their use in various applications, including vascular applications. Consequently, in the present invention steps are taken to address these shortcomings.

In the present invention, medical articles are provided, which are at least partially biodegradable within a subject. Preferred subjects (also referred to as "patients") are vertebrate subjects, more preferably mammalian subjects, particularly human subjects. These medical articles contain at least one biodegradable polymer that produces acidic molecules upon degradation. In addition, the medical articles of the invention also contain one or more acid neutralizing cationic species. As defined herein, an "acid neutralizing cationic species" is a positively charged species that is capable of providing a localized pH at the article surface (and in some instances, within the article), during biodegradation of the article, that is higher than the pH would otherwise be in the absence of the cationic species. Examples of cationic species include cationic polymers, non-polymeric cationic compounds such as cationic surfactants, and cationic nanoparticles such as cationic clays. Without wishing to be bound by theory of operation, it is believed that the acid neutralizing cationic species generally reduce the acidity of the acidic degradants by accepting acidic protons released by the degradants and/or by trapping the degradants themselves.

Medical articles benefiting from the invention include a wide variety of articles for internal medical use, including various injectable, implantable and insertable medical articles. Some specific examples include stents (e.g., vascular and non-vascular stents, such as coronary artery stents, peripheral vascular stents, urethral stents, ureteral stents, biliary stents, tracheal stents, gastrointestinal stents and esophageal stents), stent grafts, vascular grafts, vascular access ports, catheters, filters (e.g., vena cava filters), embolization devices including cerebral aneurysm filler coils, myocardial plugs, pacemaker leads, left ventricular assist hearts and pumps, total artificial hearts, heart valves, vascular valves, tissue bulking compositions, microspheres, tissue engineering scaffolds for cartilage, bone, skin and other in vivo tissue regeneration, tubes for nerve regeneration, sutures, suture anchors, anastomosis clips and rings, tissue staples and ligating clips at surgical sites, orthopedic prosthesis such as bone screws, bone grafts, bone plates, joint prostheses, as well as various other medical articles that are adapted for internal use within the body.

The medical articles of the present invention include those that are used for diagnosis, systemic treatment, or localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone. As used herein, "treatment" refers to the prevention of a disease or condition, the reduction or elimination of symptoms associated with a disease or condition, or the substantial or complete elimination of a disease or condition.

In certain embodiments, the entire medical article is biodegradable. In certain other embodiments only a portion of the medical article is biodegradable, for example, where only a component of the medical article is biodegradable or where a biodegradable coating is provided over a non-biodegradable substrate.

Hence, biodegradable medical articles and biodegradable portions of medical articles in accordance with the present invention may exist in a variety of shapes, for example, in shapes such as microspheres, fibers, threads, rods, screws, tubes, layers, plates, etc.

Biodegradable layers are advantageous that in they can be provided over an underlying substrate at a variety of locations, and in a variety of shapes (e.g., in desired patterns, for instance, using appropriate masking techniques, such as lithographic techniques), and they can be stacked. Materials for use as underlying medical article substrates include metallic and non-metallic substrates, including ceramic and polymeric substrates. The substrate material can also be a carbon- or silicon-based material. As used herein a "layer" of a given material is a region of that material whose thickness is small compared to both its length and width. A layer need not be planar, for example, taking on the contours of an underlying substrate. Layers can be discontinuous (e.g., patterned). Terms such as "film," "layer" and "coating" may be used interchangeably herein.

In the medical articles of the present invention, the cationic species may be associated with the biodegradable polymer in a variety of ways. For example, the cationic species may be blended with the biodegradable polymer. Blending is desirable in many embodiments, for example, because the cationic species and biodegradable polymer are placed in intimate association with one another. Moreover, further materials can also be provided within the blend to provide various additional functions. Such further materials include, for example, (a) agents that enhance visibility of the medical article in the body, such as radiopaque materials, MRI contrast agents, ultrasonic/ecogenic agents, and so forth, and (b) agents that can enhance the mechanical properties of the blend, for example, fillers such as carbon nanotubes, nanosilica and other nanofillers.

Other ways of associating the cationic species with the biodegradable polymer include, for example, placing a layer containing the cationic species (designated layer "A") adjacent to a layer containing the biodegradable polymer (designated layer "B"). Moreover, multiple A layers, multiple B layers, or both, may be employed, for example, in an A-B-A arrangement, an A-B-A-B arrangement, or other arrangement, depending upon application.

Various techniques are available for forming medical articles in accordance with the present invention.

For example, where the biodegradable polymer has thermoplastic characteristics, a variety of standard thermoplastic processing techniques can be used to form regions of various shapes, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire articles or portions thereof can be made.

In other embodiments, solvent-based techniques are used to form regions of various shapes. Using these techniques, a region can be formed by providing a solution or suspension that contains the biodegradable polymer, the cationic species, or both. The solvent that is ultimately selected will contain one or more solvent species, which are generally selected based on their ability to dissolve at least some of the species forming the region, as well as other factors, including drying rate, surface tension, etc. Generally, several solvents will be tested to see which provides regions having the best characteristics.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a solution (where solvent-based processing is employed) or melt (where thermoplastic processing is employed) is applied to a substrate to form a desired region. For example, the substrate can correspond to all or a portion of a medical article surface to which a layer is applied. The substrate can also be, for example, a template, such as a mold, from which the region is removed after solidification. In other embodiments, for example, extrusion and co-extrusion techniques, fiber forming techniques, etc., one or more regions are formed without the aid of a substrate.

If it is desired to provide one or more therapeutic agents (and/or any other optional agents) in the region, so long as these agents are stable under processing conditions, then they can be provided within the solution or melt and co-processed along with the other compounds. Alternatively, therapeutic and/or other optional agents may also be introduced subsequent to the formation of the region in some instances. For instance, in some embodiments, the therapeutic and/or any optional agents are dissolved or dispersed within a solvent, and the resulting solution is contacted with a previously formed region (e.g., using one or more of the application techniques described above, such as dipping, spraying, etc.).

Regions are provided over therapeutic-agent-containing regions in some embodiments of the invention (e.g., where the region acts as a barrier region, to slow the release of the therapeutic agent). In these embodiments, for example, a polymeric region can be formed over a therapeutic-agent-containing region, for instance, using one of the solvent based or thermoplastic techniques described above. Alternatively, a previously formed polymeric region may be adhered over a therapeutic agent containing region.

As noted above, the biodegradable polymers within the articles of the present invention produce acidic byproducts upon degradation. Examples of such biodegradable polymers include those that contain ester linkages, which break down into molecules containing alcohol and carboxylic acid groups (e.g., hydroxyacids), and those that contain anhydride linkages, which break down into molecules containing carboxylic acids groups (e.g., diacids), among others.

Biodegradable polymers suitable for the practice of the invention may be natural or synthetic, and they may be homopolymers or copolymers. Suitable biodegradable polymers may take on a variety of architectures, including linear, branched and cyclic architectures. "Branched architectures" as the term is used herein, include star-shaped architectures (e.g., architectures in which three or more arms emanate from a single branch point), comb architectures (e.g., architectures having a main chain and a plurality of side chains) and dendritic architectures (e.g., arborescent and hyperbranched polymers), among others. Blends of differing biodegradable polymers may also be used.

Suitable biodegradable polymers for the practice of the present invention may be selected from, for example, polyesters, polyanhydrides, amino acid based polymers, and so forth.

More specific examples can be selected from homopolymers and copolymers (and their derivatives which are formed from (or have the appearance of being formed from) one or more of the following monomers: (a) alpha-hydroxy acids such as glycolic acid (also known as glycolide in dimer form), D-lactic acid and L-lactic acid (also known as D- and L-lactide in dimer form), D-malic acid and L-malic acid, among others; (b) other hydroxyl acids, including beta-, gamma-, delta-, and epsilon-hydroxy acids, as well as hydroxy acids having multiple hydroxyl groups, among others, for example, hydroxybutyric acids such as beta-hydroxybutyric acid (also known as 3-hydroxybutyric acid), gamma-hydroxybutyric acid (also known as 4-hydroxybutyric acid, and as gamma-butyrolactone in its closed ring form), hydroxyvaleric acids such as beta-hydroxyvaleric acid (also known as 3-hydroxyvaleric acid), gamma-hydroxyvaleric acid (also known as 4-hydroxyvaleric acid), delta-hydroxyvaleric acid (also known as 5-hydroxyvaleric acid, and as delta-valerolactone in its closed ring form), hydroxycaproic acids such as epsilon-hydroxycaproic acid (also known as 6-hydroxycaproic acid, or as epsilon-caprolactone in its closed ring form), as well as D-gluconic acid and L-gluconic acid, among others; (c) ester-ethers, for instance, alkyl-substituted and unsubstituted dioxanones, such as p-dioxanone (1,4-dioxan-2-one), substituted 1,4-dioxan-2-ones (e.g., alkyl substituted 1,4-dioxan-2-ones such as 6,6-dimethyl-1,4-dioxan-2-one), substituted-1,4-dioxane-2,5-diones (e.g., 3-methyl-1,4-dioxane-2,5-dione, 3,3-diethyl-1,4-dioxan-2,5-dione and 3,6-substituted-1,4-dioxane-2,5-diones), alkyl-substituted and unsubstituted dioxepanones, including 1,4-dioxepan-2-one (including its dimmer from) and 1,5-dioxepan-2-one, among others; (d) epoxy-esters such as trimethylene carbonate (also known as 1,3-dioxan-2-one) and ethylene carbonate (also known as 1,3-dioxolan-2-one), among others; and (e) diacids including alpha,omega-bis-(carboxy)alkanes and alpha,omega-bis-(carboxy)alkenes, for instance, maleic acid (cis-1,2-ethylenedicarboxylic acid), fumaric acid (trans-1,2-ethylenedicarboxylic acid), adipic acid, suberic acid, sebacic acid, and dodecanedioic acid, aromatic diacids including bis(p-carboxyphenoxy)methane, and alpha,omega-bis-(p-carboxyphenoxy)alkanes such as 1,3-bis(p-carboxyphenoxy)propane and 1,6-bis(p-carboxyphenoxy)hexane, among others.

Even more specific examples of biodegradable polymers having acidic breakdown products can be selected from the following, among many others: (a) polyesters such as polyglycolide, poly-L-lactide, poly-D-lactide, poly-DL-lactide, poly(beta-hydroxybutyrate), poly-D-gluconate, poly-L-gluconate, poly-D,L-gluconate, poly(epsilon-caprolactone), poly(delta-valerolactone), poly(p-dioxanone), and poly(trimethylene carbonate), and polyorthoesters such as those synthesized by condensing 2,2-diethoxytetrahydrofuran and di-alcohols, among others (b) polyanhydrides such as poly(adipic anhydride), poly(suberic anhydride), poly(sebacic anhydride), poly(dodecanedioic anhydride), poly(maleic anhydride), poly[1,3-bis(p-carboxyphenoxy)methane anhydride], and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], among others; and (c) copolymers such as poly (lactide-co-glycolide), poly(lactide-co-delta-valerolactone), poly(lactide-co-epsilon-caprolactone), poly(L-lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others.

Even further specific examples of biodegradable polymers having acidic breakdown products can be selected from the following, among many others: amino acid based polymers include tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and leucine and lysine-based polyester-amides. Specific examples of tyrosine-based polymers include poly(desaminotyrosyl-tyrosine ethyl ester adipate) or poly(DTE adipate), poly(desaminotyrosyl-tyrosine hexyl ester succinate) or poly(DTH succinate), poly(desaminotyrosyl-tyrosine ethyl ester carbonate) or poly(DTE carbonate), poly (desaminotyrosyl-tyrosine butyl ester carbonate) or poly (DTB carbonate), poly(desaminotyrosyl-tyrosine hexyl ester carbonate) or poly(DTH carbonate), and poly(desaminotyrosyl-tyrosine octyl ester carbonate) or poly(DTO carbonate).

Cationic species for use in the medical articles of the invention include polycationic polymers, non-polymeric cationic compounds such as low-solubility, low molecular weight compounds, for example, phosphatidyl-choline, and cationic nanoparticles. As indicated above, such cationic species are introduced to address the acidic degradation products of biodegradable polymers, including those described above.

Consequently, such medical articles may relieve the pH burden that would otherwise be placed on acid-sensitive agents and acid-sensitive tissue in the absence of the cationic species. Furthermore, where the degradation rate is pH sensitive, for example, where the degradation rate increases with an increase in acidity (e.g., where the degradation is self-catalytic), or where the degradation rate may decrease with an increase in acidity, the degradation rate may be modulated by incorporating various types and quantities of cationic species. This type of property modulation may be achieved, for example, by simple blending, and it provides great flexibility to the biodegradable polymer platform.

Examples of cationic species for use in the present invention include (a) those that have cationic character at the time of implantation or insertion of the medical article into a patient (e.g., because they are in salt form, for instance, in the form of halide or hydrohalide salts such as chloride, bromide, hydrochloride, or hydrobromide salts, among others), (b) those that have substantially non-cationic character, but become cationic upon implantation or insertion into a patient (e.g., due to acid-base reactions that occur at physiological pH), (c) those that have substantially non-cationic character, but become cationic upon exposure to acidic species, for example, due to their release upon biodegradable polymer degradation (e.g., due to acid-base reactions occurring at low pH), (d) those that have cationic character at physiological pH, but which become more cationic upon exposure to acidic species (e.g., because the polycationic polymer contains multiple types of groups having different pK values, some of which accept protons at near-neutral physiological pH, others of which accept protons at more acidic pH).

Specific examples of cationic nanoparticles for the practice of the present invention include cationic clays, which may be selected, for example, from the intercalated clays described in U.S. Pat. No. 6,262,162, which is hereby incorporated by reference. These intercalated layered materials prepared by intercalation of a multi-charged onium ion (e.g., di-ammonium, di-sulfonium, di-oxonium; ammonium/phosphonium; ammonium/sulfonium; ammonium/oxonium; phosphonium/sulfonium; phosphonium/oxonium; sulfonium/oxonium; and mixtures thereof), and optionally a matrix polymer (e.g., an epoxy, polyamide, polyvinyl alcohol, polycarbonate, polyvinylimine, polyvinylpyrrolidone, polyethylene terephthalate, or polybutylene terephthalate), between the planar layers of a swellable layered material, such as a phyllosilicate (e.g., a smectite clay).

Suitable polycationic polymers for the practice of the present invention may be selected, for example, from homopolymers and copolymers that have, or are capable of having (e.g., via protenation), one or more of the following groups: charged amino groups, including charged primary ($-NH_3^+$), secondary and tertiary amino groups, amidinium groups, guanidinium groups, triazolium groups, imidazolium groups, imidazolinium groups, pyridinium groups, sulfonium groups, including primary ($-SH_2^+$) and secondary sulfonium groups, hydrosulfide groups, phosphonium groups, including primary ($-PH_3^+$), secondary, and tertiary phosphonium groups, isothiouronium groups, nitrosyl groups, nitryl groups, tropilium groups, iodonium groups, arsonium groups, antimonium groups, oxonium groups, and anilinium groups, among others.

Polycationic polymers suitable for the practice of the invention may be natural or synthetic, they may be homopolymers or copolymers, and they may be used singly or in blends.

Specific suitable polycationic polymers may be selected, for example, from suitable members of the following: polyamines, including polyamidoamines, poly(amino methacrylates) including poly(dimethylaminoethyl methacrylates), polyvinylamines, polyvinylpyridines, poly(vinylbenzyltrimethylamines), polyallylamines and poly(diallyldimethylamines), spermine, spermidine, polyimines including polyalkyleneimines such as polyethyleneimines, polypropyleneimines and ethoxylated polyethyleneimines, basic peptides and proteins, including polymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, poly-L,D-ornithine, gelatin, albumin, and protamine sulfate, and polycationic polysaccharides such as cationic starch, cationic dextran and chitosan, among others.

As with the biodegradable polymers described above, polycationic polymers suitable for the present invention may take on a variety of architectures, including linear, cyclic and branched architectures.

In certain beneficial embodiments, polycationic polymers for use in the present invention are dendritic polymers, or "dendrimers," which are a class of highly branched, tree-like polymers. Specific examples of polycationic dendritic polymers are polyamidoamine (PAMAM) dendrimers and polypropyleneimine (PPI) dendrimers. They are globular in shape, and they may be synthesized through step-wise, repetitive reaction sequences, starting with a core unit, and giving rise to increasing generations, with each with increasing branching and radii.

For example, in one method of forming PAMAM dendrimers, ammonia is used as a core molecule. In the presence of methanol, ammonia is capable of reacting with methyl acrylate, followed by ethylenediamine, at which point there is an amine group at the end of each branch. Each amine group can then react with two methyl acrylate monomers, followed by two ethylenediamine monomers. The number of amine groups doubles with each generation. A schematic depiction of a particular PAMAM dendrimer follows:

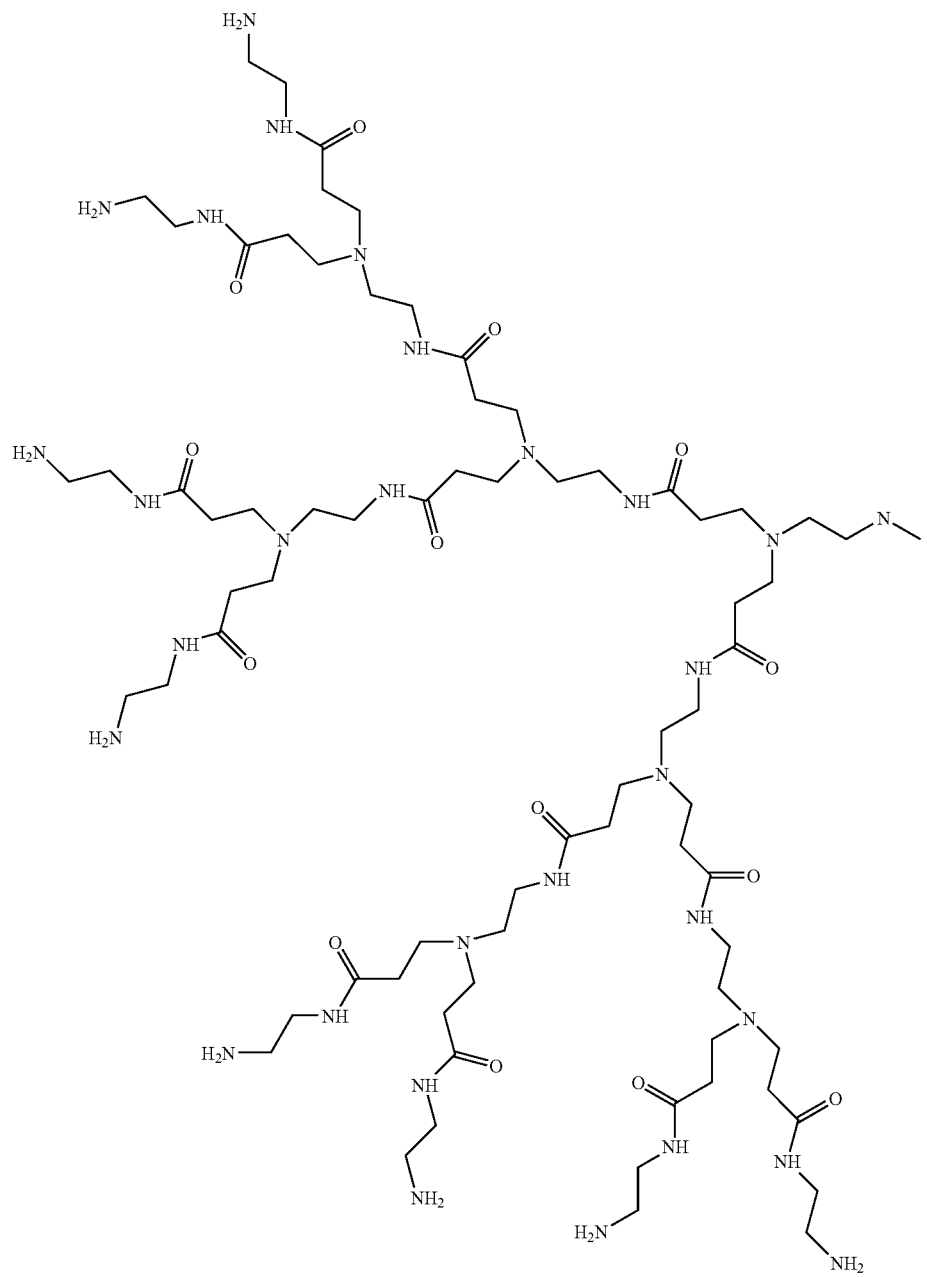

-continued

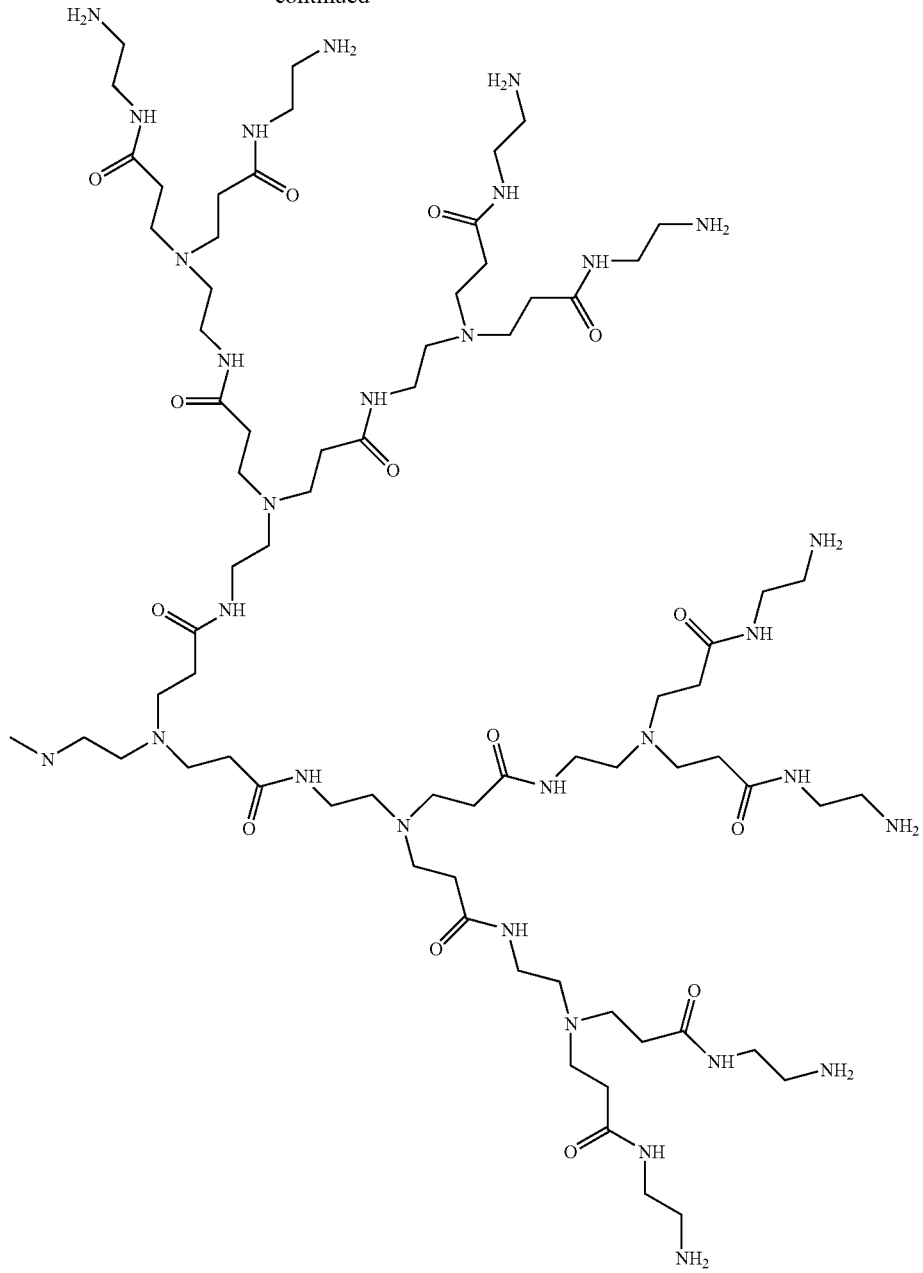

PAMAM dendrimers with primary amine endgroups are commercially available from Dendritech, Inc., Midland, Mich., USA, in generations G0 to G10, and in either water or methanol solutions.

In addition to providing a large number of functional groups (e.g., in the case of PAMAM, a large number of tertiary internal amine and amide groups, and a large number of external primary amine groups), dendrimers are also known to have internal cavities, which make it possible for them to act as hosts for various guest molecules.

Dendrimers of various generations may be used in the present invention (e.g., generations 1, 2, 3, 4, 5, 6, 7, 8, 9, 10, etc.). A limiting generation exists for each dendrimer chemistry. For PAMAM dendrimers, this limit has been reported to be ten generations. See, e.g., D. Cakara et al., "Microscopic Protonation Equilibria of Poly(amidoamine) Dendrimers from Macroscopic Titrations," *Macromolecules* 2003, 36, 4201-4207. Varying the generation will vary the number of functional groups (with higher generations providing a greater number of functional groups—e.g., for PAMAM, the number of terminal amines doubles which each generation) and will also typically vary the characteristics of the cavities within the dendrimer, thereby affecting the dendrimer's behavior as a host for guest molecules. In the present invention, the dendrimer cavities may be designed so as to trap the acidic degradation products of the biodegradable polymers.

Certain polycationic polymers, including polycationic dendrimers such as PAMAM, are only partially ionized at neutral pH. In the case of PAMAM, this dendrimer goes from a nearly non-protonated form at a pH of about 10 to a nearly completely protonated form at a pH of about 4 (with lower generations requiring slightly lower pH for full protenation than do higher generations). See, e.g., D. Cakara et al., "Microscopic Protonation Equilibria of Poly(amidoamine) Dendrimers from Macroscopic Titrations," *Macromolecules* 2003, 36, 4201-4207. Hence, PAMAM may also be thought of as a buffering agent for acidic species that are released upon degradation of the biodegradable polymer.

As a specific example, it is known that poly(lactic acid-glycolic acid) copolymers produce lactic acid and glycolic acid as degradation by-products. By associating PAMAM with this copolymer (e.g., by blending), hydrogen ions donated/produced by these acidic degradants may be accepted/captured by non-protonated amines that are present within the PAMAM dendrimer, and/or these degradants may become entrapped within the cavities of the PAMAM dendrimer. Of course, the present invention is applicable to other biodegradable polymers besides poly(lactide-co-glycolide), and other cationic species besides PAMAM may be employed, including other polycationic dendrimers, for instance poly(propylene amine) dendrimers, and other cationic species that are not dendrimers or even polymers, for example, low-solubility, low molecular weight cationic compounds and cationic nanoparticles.

As noted above, the present invention is applicable to a variety of biodegradable and partially biodegradable medical articles. As one specific example, the present invention is applicable to tissue engineering scaffolding. Since most of the cells that grow within scaffolding are sensitive to pH, the ability to neutralize the acidic effects of the biodegradable polymer is useful. In a more specific example, a blend of poly(lactide-co-glycolide) and PAMAM dendrimer may be fabricated into a 3-dimensional tissue scaffolding, which may be used to grow cardiovascular muscle from stem cells.

In certain embodiments, it may be desirable to further include therapeutic agents within the medical articles of the invention. "Therapeutic agents," "drugs," "pharmaceutically active agents," "pharmaceutically active materials," and other related terms may be used interchangeably herein. These terms include genetic therapeutic agents, non-genetic therapeutic agents and cells.

Therapeutic agents for medical articles include, for example, suitable members of those set forth in paragraphs [0040] to [0046] of commonly assigned U.S. Patent Application Pub. No. 2003/0236514, the entire disclosure of which is hereby incorporated by reference. Various specific suitable agents may be selected from the following: paclitaxel (including particulate forms thereof such as ABRAXANE albumin-bound paclitaxel nanoparticles), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, resiquimod, imiquimod (as well as other imidazoquinoline immune response modifiers), human apolioproteins, growth factors, such as vascular endothelial growth factors (e.g., VEGF-2), as well a derivatives of the forgoing, among many others.

In these embodiments, controlled release of the therapeutic agent is typically desired. Consequently, in embodiments where the therapeutic agent comes into contact with the polycationic polymer (e.g., by blending, diffusion, etc.), care is typically taken to ensure (a) that the polycationic polymer does not entrap the therapeutic agent and (b) that it does not electrostatically bind to the therapeutic agent (e.g., by using an uncharged therapeutic agent or a therapeutic agent that has a cationic charge), or otherwise chemically interact with the therapeutic agent which may hinder release, may alter the effect of the therapeutic agent, and/or may hinder the ability of the polycationic polymer to handle the acidic degradation products of the biodegradable polymer. In many embodiments, the therapeutic agent is a small-molecule drug, rather than a biopolymer such as protein (which may be negatively charged) or DNA (which is typically negatively charged).

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical article comprising
  (a) a biodegradable polymer that produces acidic molecules upon degradation within a subject; and
  (b) an acid neutralizing cationic species,
  wherein said cationic species is a polycationic polymer,
  wherein said biodegradable polymer and said acid neutralizing cationic species are blended within a polymeric region in the form of a biodegradable coating that is provided over a metallic or ceramic substrate, said medical article being an implantable or insertable medical article, and
  wherein said medical article comprises a single therapeutic agent as the only therapeutic species, which therapeutic agent is not electrostatically bound to or entrapped within said cationic species, which therapeutic agent is selected from an uncharged therapeutic agent and a cationic therapeutic agent, and which is released from said article within said subject.

2. The medical article of claim 1, wherein said biodegradable polymer is a biodegradable polyester.

3. The medical article of claim 2, wherein said biodegradable polyester is selected from poly(hydroxy acids), poly (ester-ethers), poly(epoxy-esters), poly(ester-amides), poly-phosphoesters, poly(ester-urethanes), and polyorthoesters.

4. The medical article of claim 1, wherein said biodegradable polymer is a biodegradable polyanhydride.

5. The medical article of claim 1, wherein said polymer is a homopolymer or copolymer that comprises one or more monomers selected from glycolic acid, D-lactic acid, L-lactic acid, D-malic acid, L-malic acid, beta-hydroxybutyric acid, gamma-hydroxybutyric acid, beta-hydroxyvaleric acid, gamma-hydroxyvaleric acid, delta-hydroxyvaleric acid, epsilon-hydroxycaproic acid, D-gluconic acid, L-gluconic acid, p-dioxanone, trimethylene carbonate, ethylene carbonate, maleic acid, fumaric acid, adipic acid, suberic acid, sebacic acid, dodecanedioic acid, bis(p-carboxyphenoxy)methane, 1,3-bis(p-carboxyphenoxy)propane and 1,6-bis(p-carboxyphenoxy)hexane.

6. The medical article of claim 1, wherein said biodegradable polymer is a poly(alpha-hydroxy acid).

7. The medical article of claim 6, wherein said poly(alpha-hydroxy acid) is poly(lactic acid-co-glycolic acid).

8. The medical article of claim 1, wherein said medical article comprises two or more different biodegradable polymers.

9. The medical article of claim 1, wherein said medical article comprises two or more different cationic species.

10. The medical article of claim 1, wherein said therapeutic agent is an uncharged therapeutic agent.

11. The medical article of claim 1, wherein said therapeutic agent is a cationic therapeutic agent.

12. The medical article of claim 1, wherein said substrate is a non-biodegradable substrate.

13. The medical article of claim 1, wherein said medical article is entirely biodegradable.

14. The medical article of claim 13, wherein the medical article is selected from vascular grafts, bone screws, bone grafts, bone plates, myocardial plugs, guide tubes for nerve regeneration, scaffolding for tissue engineering, and stents.

15. The medical article of claim 1, wherein said medical article is selected from vascular stents, non-vascular stents, vascular grafts, vascular access ports, vascular catheters, non-vascular catheters, filters, myocardial plugs, heart valves, vascular valves, tissue engineering scaffolds, tubes for nerve regeneration, sutures, bone screws, bone grafts, and bone plates.

16. The medical article of claim 1, wherein the medical article is selected from vascular grafts, bone screws, bone grafts, bone plates, myocardial plugs, guide tubes for nerve regeneration, scaffolding for tissue engineering, and stents.

17. The medical article of claim 16, wherein said therapeutic agent is a cationic therapeutic agent.

18. The medical article of claim 16, wherein said therapeutic agent is an acid sensitive therapeutic agent.

19. A medical article comprising:
  (a) a biodegradable polymer that produces acidic molecules upon degradation within a subject; and
  (b) an acid neutralizing cationic species which is a polycationic polymer selected from polyamines, polyimines and polycationic polysaccharides,
  wherein said biodegradable polymer and said acid neutralizing cationic species are blended within a polymeric region in the form of a biodegradable coating that is provided over a substrate, said medical article being an implantable or insertable medical article, and
  wherein said medical article comprises a single therapeutic agent as the only therapeutic species, which therapeutic agent is not electrostatically bound to or entrapped within said cationic species, which therapeutic agent is selected from an uncharged therapeutic agent and a cationic therapeutic agent, and which is released from said article within said subject.

20. The medical article of claim 19, wherein said polycationic polymer is selected from polyamidoamines, polyalkyleneimines, and chitosan.

21. A medical article comprising
  (a) a biodegradable polymer that produces acidic molecules upon degradation within a subject; and
  (b) an acid neutralizing cationic species in the form of a polycationic dendrimer,
  wherein said biodegradable polymer and said acid neutralizing cationic species are blended within a polymeric region, said medical article being an implantable or insertable medical article, and
  wherein said medical article comprises a single therapeutic agent as the only therapeutic species, which therapeutic agent is not electrostatically bound to or entrapped within said cationic species, which therapeutic agent is selected from an uncharged therapeutic agent and a cationic therapeutic agent, and which therapeutic agent is released from said article within said subject.

22. The medical article of claim 21, wherein said polycationic dendrimer is selected from polyamidoamine dendrimers and polyalkyleneimine dendrimers.

23. The medical article of claim 21, wherein said biodegradable polymer is a poly(alpha-hydroxy acid).

* * * * *